(12) United States Patent
Naumann et al.

(10) Patent No.: US 7,351,988 B2
(45) Date of Patent: Apr. 1, 2008

(54) BEAM ALLOCATION APPARATUS AND BEAM ALLOCATION METHOD FOR MEDICAL PARTICLE ACCELERATORS

(75) Inventors: Jakob Naumann, Darmstadt (DE); Klaus Poppensieker, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 340 days.

(21) Appl. No.: 11/131,978

(22) Filed: May 18, 2005

(65) Prior Publication Data

US 2006/0113487 A1 Jun. 1, 2006

(30) Foreign Application Priority Data

May 19, 2004 (DE) ............... 10 2004 025 263
Jun. 2, 2004 (DE) ............... 10 2004 027 071

(51) Int. Cl.
*A61N 5/00* (2006.01)
*G21G 5/00* (2006.01)

(52) U.S. Cl. ............... 250/492.3; 250/492.1; 250/492.2; 250/394; 250/398; 328/233; 328/234; 328/235; 364/413.14; 364/413.15

(58) Field of Classification Search ......... 250/492.3, 250/492.2, 492.1, 394, 398; 328/233, 234, 328/235; 364/413.14, 413.15
See application file for complete search history.

(56) References Cited

U.S. PATENT DOCUMENTS

| 5,260,581 | A | 11/1993 | Lesyna et al. |
| 5,895,926 | A | 4/1999 | Britton et al. |
| 6,509,573 | B1 * | 1/2003 | Badura et al. ........... 250/492.3 |
| 6,683,318 | B1 * | 1/2004 | Haberer et al. ......... 250/492.3 |

* cited by examiner

*Primary Examiner*—Jack Berman
*Assistant Examiner*—Meenakshi S Sahu
(74) *Attorney, Agent, or Firm*—Frommer Lawrence & Haug LLP; Ronald R. Santucci (57) ABSTRACT

The invention relates to a beam allocation apparatus (21) for medical particle accelerators and also to a beam allocation method. This beam allocation apparatus (21) should manage a plurality of control rooms (8-12) for different treatment rooms and for quality assurance rooms and control rooms for the particle accelerator (1) and co-ordinate the assignment of beam sovereignty. For the purpose, the beam allocation apparatus (21) has an arbitration unit (26) having switching logic (27) and monitoring unit (28) and also a sequence control (29). The latter are provided, by way of signal lines (30), with a spill abort system (31) for aborting ion beam irradiation within micro-seconds. For the purpose, the spill abort system (31) has at least one spill abort magnet (32). For the purpose, the beam allocation apparatus (21) provides direct access from one of the control room (8-12) of the irradiation-active treatment room for aborting the particle beam within micro-seconds.

21 Claims, 7 Drawing Sheets

BEAM ALLOCATION APPARATUS AND BEAM ALLOCATION METHOD FOR MEDICAL PARTICLE ACCELERATORS

This application claims priority benefits from German Patent Application Number 10 2004 025 263.7 filed May 19, 2004 and German Patent Application Number 10 2004 027 071.6 filed Jun. 2, 2004.

The invention relates to a beam allocation apparatus for medical particle accelerators and also to a beam allocation method.

A beam allocation apparatus and a beam allocation method for medical particle accelerators are known from the publications U.S. Pat. No. 5,260,581 and U.S. Pat. No. 5,895,926.

A method of treatment room selection verification in a beam therapy system is known from the publication U.S. Pat. No. 5,260,581. The method compares treatment room request signals with an irradiation path configuration signal from a control room which controls the path of the beam transported from an accelerator to one of the treatment rooms. Upon agreement of the request and beam path signals, transport to a selected treatment room is authorised. For the purpose, the beam path for each of the treatment rooms has deflection magnets, which in a first state of the deflection magnet deflect the accelerated beam from a transport path to the treatment station and in a second state of the deflection magnets deflect the beam into a treatment-free collection space.

A method and apparatus for beam security in a beam treatment facility is known from the publication U.S. Pat. No. 5,895,926. The system monitors and controls the radiation steering systems to safeguard them against wrong-path and multiple-path conditions which can lead to an accidental radiation incident. For that purpose, in the method, the configuration of the beam path signals is compared to signals of a requested beam configuration in order to check for agreement. Special attention is paid therein to ensuring that overheating does not occur and that unauthorised personnel cannot intervene in the path conditions.

In the case of such methods, transfer of the radiation to the treatment room is made possible only in authorised cases. For aborting treatment, each of the treatment rooms has, by means of its control room, direct access, which has been assigned to it, to individual deflection magnets in the transport path of the ion beam to the treatment rooms. The inertia of the deflection magnets, especially their self-induction characteristics, allows the beam feed to be aborted within about 500 ms. However, for ion beam treatment which is not based on area-wise illumination of the tumour tissue as in the prior art but rather on point-wise coverage of the tumour tissue by means of a scanning method (for example, a raster scanning method), such switch-off times by means of deflection magnets in transport paths of the highly accelerated ion beam are not acceptable.

An ion or proton beam that is suitable for the purposes of beam therapy necessarily comprises ionising radiation under the terms of radiation protection regulations and accordingly is also potentially hazardous to humans. Therefore, there must be complete assurance in such facilities that the beam from the accelerator can reach an irradiation room only at a defined point in time and in a defined manner. For point-wise scanning irradiation, therefore, the possibility must exist for aborting the beam procedure within the shortest time of a few hundred micro-seconds and of initiating a "spill abort" when, for example, the quality of beam delivered by the accelerator deteriorates.

On the other hand, for reasons of acceleration technology, there is the requirement that beam guidance elements which could carry out such a rapid beam abort and which could therefore form an improved "spill abort system" are not, or cannot be, provided for each irradiation/control room separately. In a beam therapy facility, the actual acceleration region (for example, in the form of a synchrotron, cyclotron or linear accelerator; the term "acceleration region" also being used hereinbelow for those components that immediately follow on from the acceleration region and that are common to a plurality of treatment rooms), which has such a sufficiently rapid "spill abort system", is not provided a number of times but rather serves a plurality of treatment rooms so that each treatment room does not have its own acceleration region (for example, its own synchrotron) for a rapid "spill abort".

There exist, world-wide, a small number of medical radiation devices having one particle beam for a plurality of treatment rooms, but none of those facilities uses a scanning method in which an ion beam scans tumour tissue point-wise with the correspondingly high demands on the behaviour of a "spill abort system" in terms of time. Typically, the elements used for safety functions in the prior art, namely the deflection magnets of the individual irradiation positions, are too slow for scanning methods. Utilising elements that are necessarily held in common is not possible in the case of the methods known hitherto and the beam allocation apparatuses known hitherto. Uncontrolled simultaneous intervention by a plurality of treatment rooms does not allow regulated operation and is potentially hazardous for the patient.

The problem of the invention is to provide a beam allocation apparatus that prevents, in a manner relevant to safety under the terms of medical product statute, the simultaneous access from a plurality of control rooms of corresponding treatment rooms or quality assurance rooms to components of a particle accelerator that are used in common and that especially excludes the possibility of simultaneous intervention by a plurality of control rooms in the "spill abort system" of an acceleration region. The problem of the invention is, furthermore, to provide a switching unit which, in a manner relevant to safety, regulates beam sovereignty for a plurality of control rooms having equal rights.

In addition, the problem of the invention is to allow beam sovereignty during clinical operation in a predetermined sequence for making optimum use of the accelerator to its full capacity and also to allow an immediate response to an emergency. Finally, the problem of the invention is to provide a switching unit which assigns beam sovereignty using a few components that are relevant to safety in order to keep to a low level the outlay that is required for certification within the framework of an EU conformity assessment procedure for the purpose of obtaining a licence as a medical device in accordance with medical device statute.

The problem is solved by the subject-matter of the independent claims. Advantageous developments of the invention are to be found in the dependent claims.

In accordance with the invention, a beam allocation apparatus for medical particle accelerators is provided. The particle accelerator has at least one acceleration region, a transport path and deflection components, by way of which a plurality of treatment rooms, each having a control room, are supplied with a particle beam comprising ion packets.

The beam allocation apparatus according to the invention has an arbitration unit having switching logic, monitoring unit and sequence control, which is in electrical communication, by way of signal lines, with a spill abort system, which has at least two rapid spill abort elements in the acceleration region or in the beam guidance common to all the irradiation positions. For the purpose, the beam allocation apparatus provides direct access from the control room of the irradiation-active irradiation room to the spill abort system of the acceleration region in order to accomplish particle beam aborting within micro-seconds in the event of danger.

The radiation allocation apparatus according to the invention has the advantage that it not only allows the customary possibilities for access to and for acting on the deflection magnet associated with each irradiation room but in addition allows, in the event of danger, an aborting of beam treatment that is more rapid by several orders of magnitude, by means of the fact that beam sovereignty and access to the spill abort system of the acceleration region is allocated by the apparatus to the control room of the particular irradiation-active treatment room. Accordingly, access to the spill abort system is regulated in a manner relevant to safety by an entity, namely that of the arbitration unit, which makes possible more rapid beam aborting and prevents simultaneous intervention by a plurality of control rooms in the spill abort system. At the same time, the beam allocation apparatus according to the invention allows beam sovereignty to be assigned in the sequence of irradiation-active control rooms and within the said access time it allows an immediate response to be made to an emergency. Furthermore, as a result of the fact that assignment of access entitlement is concentrated in one arbitration unit having switching logic, monitoring unit and sequence control, the number of components that are relevant to safety is extremely small so that the outlay that is required for certification within the framework of an EU conformity assessment procedure for the purpose of obtaining a licence as a medical device in accordance with medical device statute remains low.

The spill abort system has at least one spill abort magnet as spill abort element. In addition, the beam allocation apparatus has access to an exciter of the acceleration region.

In a preferred embodiment of the invention, each control room of a treatment room and/or of a quality assurance room and/or of a particle accelerator has a request signal line to the switching logic of the arbitration unit for requesting transfer of beam sovereignty to the control room together with access entitlement to the exciter and/or the spill abort magnet of the acceleration region. This embodiment of the invention has the advantage that, by way of preparation, the beam allocation apparatus can, on the basis of the request signal line to the switching logic of the arbitration unit, prepare a sequence from among control rooms having equal rights and a time sequence of access entitlements.

By way of a further signal line—the so-called grant signal line—leading to the control room, confirmation is given to the control room, following feedback from the spill abort system of the acceleration region, of delivery of the request and incorporation in a queue. A third signal line between the control room and the switching logic of the arbitration unit—a so-called clear signal line—serves for actively signalling from the control room the end or the temporary relinquishment of beam sovereignty and therefore for actively returning to the arbitration unit the power to allocate beam sovereignty.

The control room is connected to the switching logic of the arbitration unit by way of a fourth line in order, by means of that line, the so-called "spill pause line", to initiate interruption of beam supply. In the process, the aborting of irradiation is brought about by direct access of the control room to the exciter and/or the spill abort magnet of the acceleration region. For the control room of the irradiation-active treatment room this spill pause line accordingly has the advantage that a beam abort is performed within a few micro-seconds. Spill pauses are generated in the regular course of events during irradiation using scanning methods and consequently do not represent an error state.

A fifth connection between the control room and the switching logic of the arbitration unit consists of an interlock line, by means of which an irradiation abort is carried out by direct access of the control room to the exciter and/or the spill abort magnet of the acceleration region whilst maintaining access reservation. This interlock line is activated whenever an acute but relatively short-term emergency occurs, for example in the case of unexpected displacement of the position of the measured beam position in the irradiation room.

In a further embodiment of the invention, in addition to those five connections between the control room and the switching logic of the arbitration unit, provision is made for the control rooms to have access, independently of the arbitration unit, serially, by means of a potential-free interlock line, to the spill abort system of the acceleration region. For that purpose, the potential-free switches of all the control rooms are serially connected and closed so that, on actuation of the switch by one of the control rooms, an immediate spill abort can be carried out by means of this redundant signal path. The serial connection of the potential-free interlock line means that, irrespective of beam allocation, each irradiation position can force an irradiation abort when the primary signal path of the spill abort system or the arbitration unit itself fails.

In accordance with the connections between the switching logic and the control rooms there are corresponding electrical connections between the switching logic of the arbitration unit and the spill abort system of the acceleration region. Because there are present in each case a request signal line, a grant signal line, a spill pause line and an interlock line both to the exciter and to the spill abort magnet, the number of signal lines between the switching logic of the arbitration unit and the spill abort system is doubled, as a result of which system safety is further increased.

The monitoring unit of the arbitration unit receives signals, preferably by way of input signal connections, from the switching logic and the sequence control and is connected, by way of output connections, to the spill abort system of the acceleration region. By means of those lines, the monitoring unit of the arbitration unit checks whether more than one request entities have received a grant signal or whether a grant signal is present for a beam target without an associated request signal or whether a grant signal is present for a beam target even though that beam target does not correspond to the sequence control instruction. In the aforesaid cases, a spill abort is normally immediately initiated by way of a redundant signal path.

In a further embodiment of the invention, a scheduler is connected to the switching logic of the arbitration unit and, by way of the sequence control, the arbitration unit controls the working-through of a queue of irradiation requests, which is produced in the scheduler. A scheduler of such a kind can comprise a computer or a number of microprocessors; it serves for optimisation of the input data and checks the presence of irradiation plans and the correctness of beam assignment. In addition, the scheduler supports representation of the queue in all the control rooms, supplies a progress display, provides warning signals and carries out updating of the queue. In addition, it checks the availability of request entities or availability of control rooms, provides a return signal for scheduling and regulates access rights of the different control rooms. Despite those many and various tasks of the scheduler, the scheduler, together with its connections, does not belong to that part of the beam allocation apparatus according to the invention which is relevant to safety but rather is an addition so that, in the event of failure of the scheduler or absence of the scheduler in a beam therapy facility, the arbitration unit applies a method wherein the control rooms and, accordingly, the request units in turn are given the opportunity to make an ion beam reservation.

Preferably, the exciter is a high-frequency resonance component for ion packets in the coupling-in region of a synchrotron serving as the acceleration region so that, as a result of variation or mismatching of the resonance tuning, a rapid beam abort can be initiated at the exciter in microseconds. On the other hand, the spill abort magnet is a beam guidance magnet in the coupling-out region of a synchrotron serving as the acceleration region, by means of which magnet it is possible to prevent coupling-out of the beam from the acceleration region in a few micro-seconds. Both components, which practically are available to all the control rooms in common, have the advantage that they can shorten a beam abort by several powers of ten compared to customary beam allocation apparatuses and can consequently provide a therapy system based on scanning methods (for example, raster scanning methods) with increased safety of beam protection.

In a further preferred embodiment, the beam allocation apparatus has a control and management means for allocation of a particle beam of an irradiation system for a raster scanning method having an ion writing beam of an ion beam scanning apparatus for a target volume. A system of such a kind is currently being built in Heidelberg and has hitherto only been available as a research and development system in Darmstadt at the Gesellschaft für Schwerionen.

A beam allocation method for medical particle accelerators comprises the following method steps:

Firstly, reservation of particle beam sovereignty, especially reservation of direct access to a spill abort system of the acceleration region used by all the treatment rooms, is requested by one of the control rooms for a planned irradiation duration. Then, safety-relevant reservation of the spill abort system is carried out by an electronic switching logic of an arbitration unit. Finally, the reservation is reported to each control room with permission for only one control room to carry out a beam abort by means of the spill abort system.

Furthermore, a direct and redundant signal path, which is independent of the arbitration unit, leading to the spill abort system of the acceleration region is held in a state of readiness for the control rooms, the switching elements of the control rooms being connected in series. In the process, in the event of simultaneous beam reservation requests from a plurality of control rooms, the arbitration unit decides which control room of an irradiation position can make the reservation. Despite the loss of a reservation, a spill abort can be initiated from each control room by way of the redundant signal path.

This method has the advantage of double safety in that, on the one hand, by means of superordinate entities of the arbitration unit, a spill abort can be performed only when the control unit or control room has actively made a request by way of its request line and has received a grant signal in the form of a return signal by way of the grant line. This is associated with the advantage that a control room is not given the possibility of spill aborting in unprepared and uncontrolled manner. Accordingly the possibility is also prevented of a plurality of control rooms initiating a spill abort simultaneously, especially as it is ensured by means of the arbitration unit that only the control room of an irradiation-active irradiation room is given access to the rapid beam abort system of the acceleration region. The redundant signal path, by means of which a control room can initiate a spill abort independently of the arbitration unit, is protected by serial arrangement of the switching elements for the control rooms against simultaneous contradictory access of a plurality of control rooms to the spill abort system—by that means, therefore, each irradiation position is at all times capable of switching off the beam; on the other hand, switching back on again requires the co-operation of all irradiation positions that have brought about an abort.

In a further example of implementation of the method, beam sovereignty is transferred from an active control room to another control room only when the current control room actively relinquishes control over the particle beam. This has the advantage that unprepared automatic transfer of beam sovereignty to another control room is not possible. The acceleration region is accordingly protected against simultaneous access by a plurality of control rooms to the spill abort system. Moreover, the possibility exists of the spill abort system of the acceleration region being used for switching off the beam for a short period. This is carried out by way of the interlock line and the consequence thereof is that as soon as the fault has been removed irradiation can be continued without the control room relinquishing beam sovereignty or without, in the meantime, beam sovereignty being transferred to another control room. Provision is also made for the arbitration unit to allow a control room for the particle accelerator to make a reservation for the spill abort system. The control room of the accelerator has access to all beam guidance regions for which it is ensured that no patient is present.

Because the control room for the particle accelerator is in communication in principle with all components of the acceleration region and has access thereto, the provision of reservation of access to the spill abort system for the control room of the particle accelerator is nevertheless worthwhile in order that the request from the control room of the particle accelerator can be included in the queue, which is worked through by the arbitration unit, and in order to ensure optimum use of the irradiation system. Furthermore, provision is made for the status of all reservations, access entitlements and acknowledgements to be checked by a monitoring unit of the arbitration unit and, in the event of inconsistency, for switching-off to be carried out by way of the redundant signal path. This has the advantage that no unforeseeable access conflicts can occur because the monitoring unit checks the status of all reservations, access entitlements and acknowledgements and, for safety's sake, brings about a beam abort before major damage is caused.

Furthermore, provision is made, by means of a non-safety-relevant microprocessor system which functions as a scheduler, for a sequence of reservation allocation of the spill abort system to be reported to the arbitration unit. When the microprocessor system is absent or when allocations are absent, provision is made for the arbitration unit to give the control rooms, in turn, the opportunity to make a reservation. By means of that method step it is ensured that, in all cases, the arbitration unit adequately and in a manner relevant to safety provides the control rooms with access to the rapid spill abort system.

The invention will now be explained in greater detail with reference to the accompanying Figures.

Figure 1:
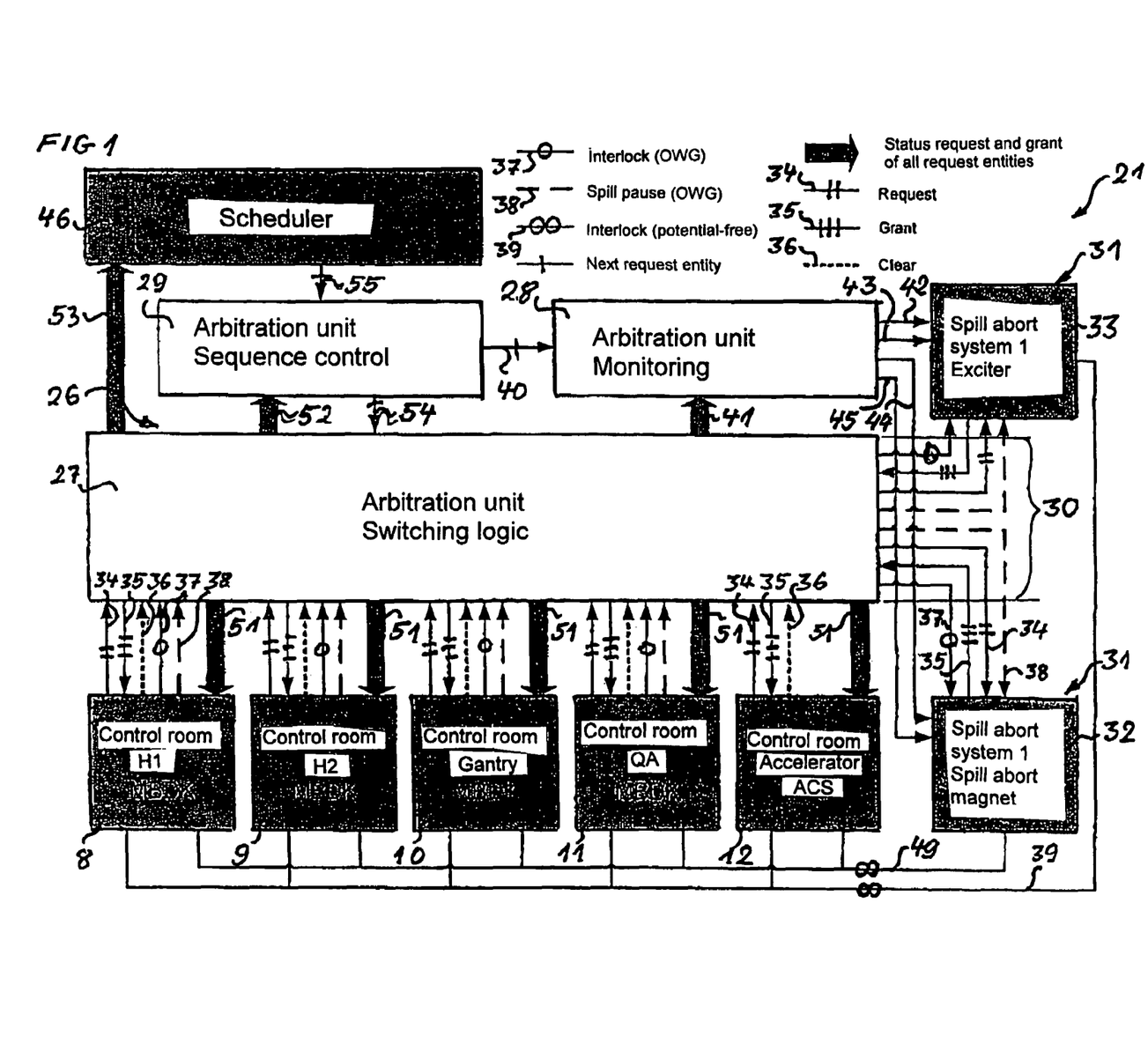
FIG. 1 is a schema of a generalised circuit diagram of a beam allocation apparatus according to an embodiment of the invention.
Figure 2:
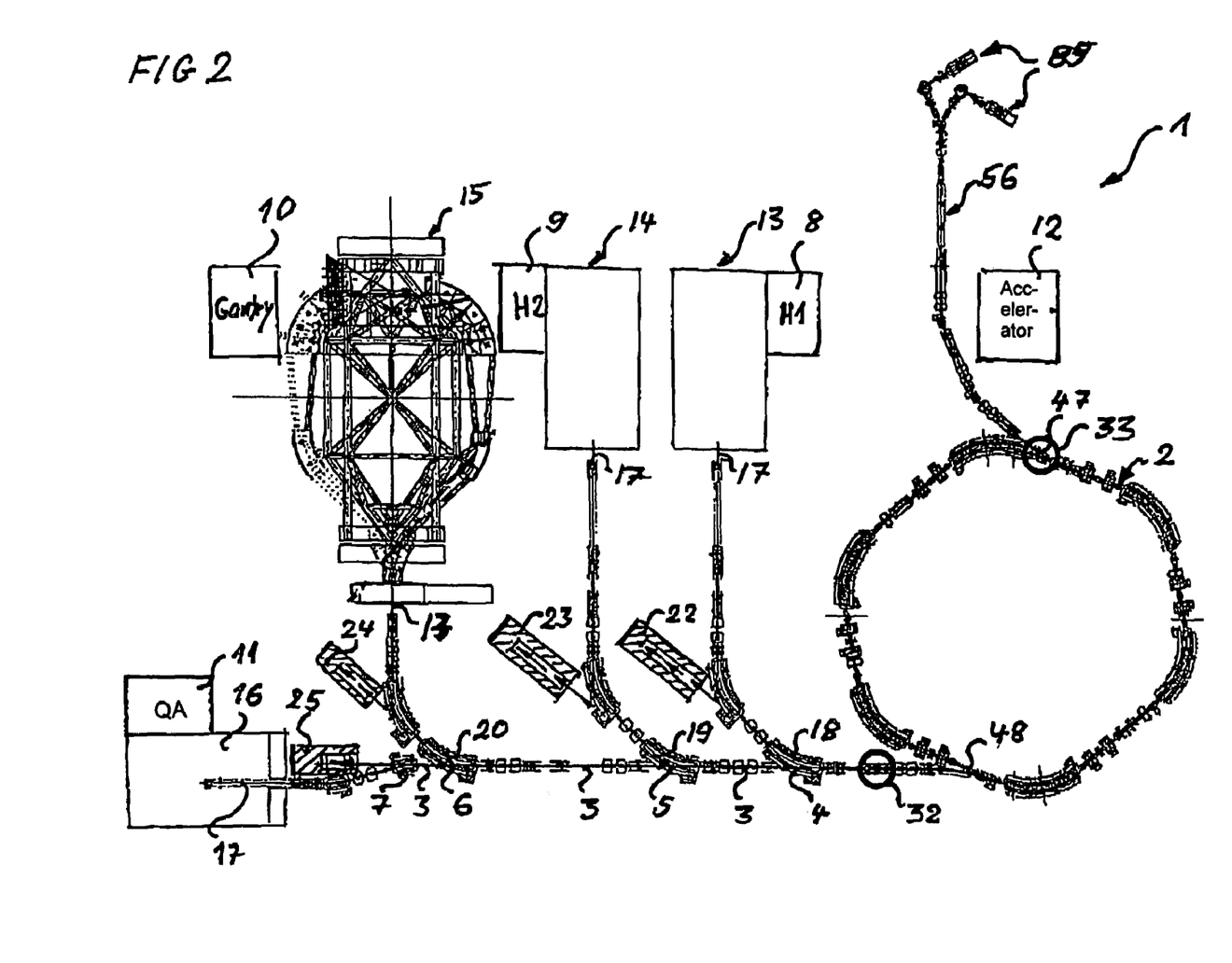
FIG. 2 is a generalised representation of a particle accelerator having components which are accessed by the beam allocation apparatus.

FIG. 1 is a schema of a generalised circuit diagram of a beam allocation apparatus 21 in accordance with an embodiment of the invention. The beam allocation apparatus 21 comprises an arbitration unit 26 having three switching blocks, namely a switching logic 27, a monitoring unit 28 and a sequence control 29. The control rooms 8-12 of various request entities are electrically connected to the switching logic 27 by way of bus lines 51 and special lines 34-38. The various request entities in this exemplified embodiment of the invention are three treatment rooms, which in FIG. 2 are denoted by the reference numerals 13-15, of which treatment room 15 is associated with a gantry by means of which the angle of ion beam entry into the patient can be varied through 360°. A further control room 11 is provided for quality assurance QA in a quality assurance room 16 shown in FIG. 2, and a fifth control room 12 is associated with the accelerator.

The switching logic 27 of the arbitration unit 26 has, by way of signal lines 30, access to the spill abort system 31 of the acceleration region. The spill abort system 31 of the acceleration region has two components, namely an exciter 33 and the spill abort magnet 32, to which the signal lines 34, 35, 37 and 38 in each case lead.

The monitoring unit 28 of the arbitration unit 26 has an input signal connection 40 from the sequence control 29 of the arbitration unit 26 and has input signal connections 41 in the form of a signal bus from the switching logic 27 of the arbitration unit 26. Furthermore, the monitoring unit 28 of the arbitration unit 26 has four output signal connections 42-45. The sequence control 29 of the arbitration unit 26 is in communication with the monitoring unit 28 by way of the input signal connection 40 of the latter and is connected to the switching logic 27 of the arbitration unit 26 by way of a bus 52 and an output signal line 54.

Whereas the hitherto mentioned signal lines are relevant to safety under the terms of the medicines statute, the arbitration unit 26 of this beam allocation apparatus 21 is in communication with a scheduler 46, which is connected to the switching logic 27 by way of a bus line 53 and which can act on the sequence control 29 of the arbitration unit 26 by way of an output signal line 55. Those signal lines 53 and 55 and also the scheduler 46 itself are not relevant to safety so that, when a scheduler 46 is absent or when a scheduler 46 has failed, the arbitration unit 26 gives the control rooms 8-12, in turn, the opportunity to exchange signals with the arbitration unit 26 or the switching logic 27 of the arbitration unit 26 by way of the signal buses 51 and the special lines 34-38.

Furthermore, by way of the redundant signal paths 39 and 49, each control room has direct access to the spill abort system 31, the redundant signal path 49 providing access to the spill abort magnet 32 and the redundant signal path 39 providing access to the exciter 33 for the control rooms 8-12. In order to ensure that a plurality of control rooms 8 to 12 do not simultaneously access the spill abort system 31, access switching elements in the control rooms 8-12 are connected in series to the redundant signal paths 39 and 49 so that, in the event of initiation of an interruption of the access switching elements by one of the control rooms 8 to 12, the other control rooms can no longer access the spill abort system 31.

The spill abort system 31 uses, in this irradiation technique, a total of 4 elements, of which, however, only 2 elements, namely the exciter 33 and the spill abort magnet 32, are shown in the generalised circuit diagram. Two of the said elements (two deflection magnets for each irradiation position) do not belong to the acceleration region but are deflection components 4 to 7, as shown in FIG. 2, which deflect the beam from a transport path towards the particular irradiation room requesting it. They are consequently directly confirmed by the particular control room 8 to 12 of an irradiation room. They are therefore controlled directly, for an abort, by the particular control room 8 to 10 of an irradiation room where irradiation is to be carried out.

The other two elements, shown as the exciter 33 and the spill abort magnet 32 in the generalised circuit diagram, are, however, arranged in the beam guidance region which is common to all irradiation stations, and they are therefore subject to the control of the various irradiation rooms in turn. Switching-over of control is carried out by means of the arbitration unit 26 according to the invention, allocation of the spill abort system 31, as shown by the generalised circuit diagram of FIG. 1, being highly relevant to safety under the terms of the radiation protection statute for medical facilities. Therefore, in the generalised circuit diagram of FIG. 1, the arrangement and distribution of the signal lines 34-38 are explicitly indicated, reference numeral 34 denoting a request line, reference numeral 35 denoting a grant line, reference numeral 36 denoting a clear line, reference numeral 37 denoting an interlock line and reference numeral 38 denoting a spill pause line.

The scheduler 46 of the generalised circuit diagram of FIG. 1 does not belong to the components of the beam allocation apparatus 21 which are highly relevant to safety although from a logical point of view it has a close connection with the arbitration unit 26. The planned sequence of irradiations is determined by a queue, which is managed by a central irradiation technique computer, the so-called scheduling computer. The associated scheduling application is accessible from all 4 local control rooms 8 to 11, the accelerator control room 12 and from various other computers of a hospital network.

The planned sequence of irradiations changes constantly in the course of a day. For the purpose, the scheduling application checks the existing sequence in the event of any change made by the user and, after every irradiation, amends it where necessary and accordingly corrects the estimates for the planned start of irradiation of an area. These changes normally fluctuate only in the range of a few minutes over a day. Under those conditions, the scheduler 46 of the arbitration unit 26, by way of its output signal line 55, provides the sequence control 29 of the arbitration unit 26 with an instruction for the next particular allocation of beam sovereignty.

The user request for beam allocation is made from the control room 8-12 in question. This request is acknowledged by the arbitration unit 26. The spill abort system 31 then has to be reserved for that irradiation position of the control room, for example control room 8. Beam allocation must be confirmed by the control room 8-12 in question. Without acknowledged allocation rights, irradiation is not started. During irradiation, access rights cannot be and must not be given back. After completion of irradiation, the access rights must, however, be actively given back to the arbitration unit 26 by the control room 8.

When a scheduling application is not available, operation is nevertheless maintained by means of the arbitration unit 26. When a scheduling application is available, the allocation rights are issued in accordance with that application. Should that not, however, be possible, rights are issued by the method wherein the arbitration unit 26 gives the control rooms 8-12, in turn, the opportunity of reserving access rights. In addition, the awarding of an access right to an irradiation position is reported to the accelerator control system or accelerator control room 12. For safety reasons, the request entities and their control rooms 8-12 receive no access rights when the arbitration unit 26 is switched off or not functioning, which means that the entire system is at a standstill. This measure is necessary because the arbitration unit 26 manages the spill abort system 31 of the acceleration region. Without access to this rapid abort system, irradiation is neither permitted nor, by virtue of the arbitration unit 26 according to the invention, possible. With the arbitration unit 26 there is additionally provided a testing possibility for function verification.

Because the accelerator having the control room 12 can have control over the spill abort system 31 given to it by the arbitration unit 26, the control rooms 8 to 12 are also referred to hereinbelow as request entities. In this exemplified embodiment of the invention, the term request entities denotes the totality of four irradiation positions, insofar as they are under the control of the irradiation technique control and safety systems, and the accelerator as fifth request entity. Control of the accelerator encompasses all beam guidance parts explicitly enabled for the accelerator and also all irradiation positions that are under the control of the accelerator control system.

With reference to the generalised circuit diagram of FIG. 1, a reservation sequence comprises the following steps.

When a request entity or a control room 8 to 12 has made in principle all arrangements for starting an irradiation, a request is sent to the arbitration unit 26 in the form of a request signal by way of the request line 34 either by pushing a button on a control room panel or by means of a signal generated by a computer. A visual display of that request is provided for, especially, the users in the control room of the irradiation-active treatment room but also the staff in other control rooms 8-12.

In order for the request entity to be given sovereignty over the spill abort system 31, several conditions have to be met:

Firstly, no other request entity has sovereignty over the spill abort system 31 of the acceleration region. Sovereignty over the spill abort system 31 is not re-assigned until the current request entity with its irradiation-active irradiation room itself actively relinquishes control.

The scheduler 46 has to specify the request entity as the next target. Should, however, the scheduler be deactivated, the access rights are offered to the request entities in turn by the arbitration unit 26.

The spill abort system 31 must be in a state of readiness in order for a request entity to be given sovereignty over the spill abort system 31.

Successful reservation of access to the spill abort system 31 is acknowledged by both elements, namely the exciter 33 and the spill abort magnet 32, of the spill abort system 31, in the form of a grant signal by way of the grant lines 35. A visual display of that reservation is provided for, especially, the users of the local control room but also the staff in all other control rooms 8-12.

Whilst irradiation is continuing, that is to say when an irradiation room is irradiation-active, the request entity can at any time switch off the two components of the spill abort system 31 with the aid of a spill pause line 38 and, alternatively, by way of a redundant signal path 39 or 49 of an interlock line.

After the end of an irradiation, the request is explicitly taken back by the request entity or control room 8-12 by means of a clear signal by way of the clear line 36. At the same time, this also deletes the grant signal.

FIG. 2 is a generalised representation of a particle accelerator 1 having components to which the beam allocation apparatus 21 according to FIG. 1 has access. The particle accelerator 1 has an acceleration region 2 in the form of a synchrotron, which accelerates ion packets to energies of about 4500 MeV. These ion packets are produced in an ion source 89 and pre-accelerated by means of a linear accelerator 56 and, in a coupling-in region 47, in which the exciter 33 is also arranged, they are coupled into the accelerator ring 2.

The exciter 33 is a high-frequency resonance component in that coupling-in region 47 of the accelerator 2 and can initiate a beam abort in micro-seconds as a result of variation or mismatching of the resonance tuning. Arranged in a coupling-out region 48 of the accelerator ring 2 is the spill abort magnet 32, which, like the exciter 33, can be used for a rapid beam abort during ion beam treatment in the raster scanning method in a manner relevant to safety. Arranged in a transport path 3 of the particle beam 17 are deflection magnets 18 to 20 for each irradiation room 13-15, which magnets deflect the ion beam 17 to the irradiation rooms 13-15. Associated with the irradiation rooms 13-15 are the control rooms 8-10, which can act directly on the deflection magnets 18-20 and can bring about a beam abort to the collection chambers 22-25 in a few hundred milli-seconds. These deflection components 4-7 of the transport path 3 are therefore not as rapid as the beam abort possibilities by means of the spill abort components 32 and 33 in the irradiation ring 2.

Figure 3:
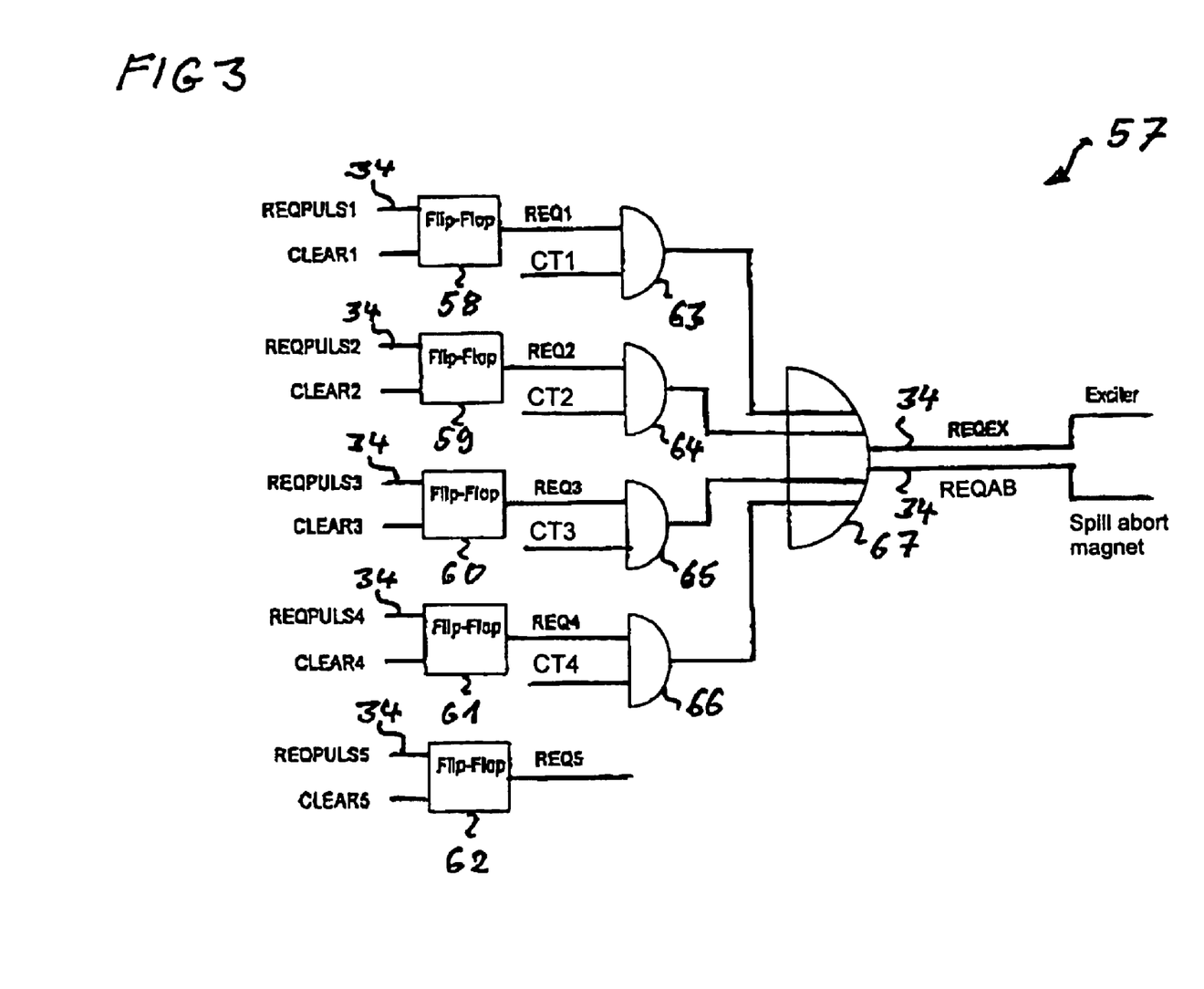
FIG. 3 is a generalised representation of a request circuit for processing request signals by way of request lines.

FIG. 3 is a generalised representation of a request circuit 57 for processing request signals REQPULS1-REQPULS5 by way of request lines 34 from the control rooms 8-12 shown in FIGS. 1 and 2. The request circuit 57 ensures that only the request signal from that request entity or control room which is currently seen as being active by the sequence control of the arbitration unit is forwarded to the exciter 33 or spill abort magnet 32 shown in FIGS. 1 and 2.

When the request entity is the control room of the accelerator itself, no reservation is made because the exciter and spill abort magnet can in any case be controlled by the accelerator. Accordingly, the request signals REQPULS1 to REQPULS5 are applied to flip-flops 58-62 of the switching logic of the arbitration unit, the flip-flops 58-62 having been returned to neutral beforehand, by means of the inputs CLEAR1-CLEAR5. The outputs of the flip-flops 58-61 are passed to logic ANDGATEs 63-66 and, by means of second inputs CT1 to CT4 of the ANDGATEs 63-66, only those requests are forwarded which, with the second input, have a confirmed active beam target CT. The outputs of the AND-GATEs 63-66 are passed to an ORGATE 67, the outputs REQEX and REQAB of which are connected in each case by way of a request line 34 to the exciter and to the spill abort magnet, respectively, of the spill abort system of the accelerator ring.

Figure 4:
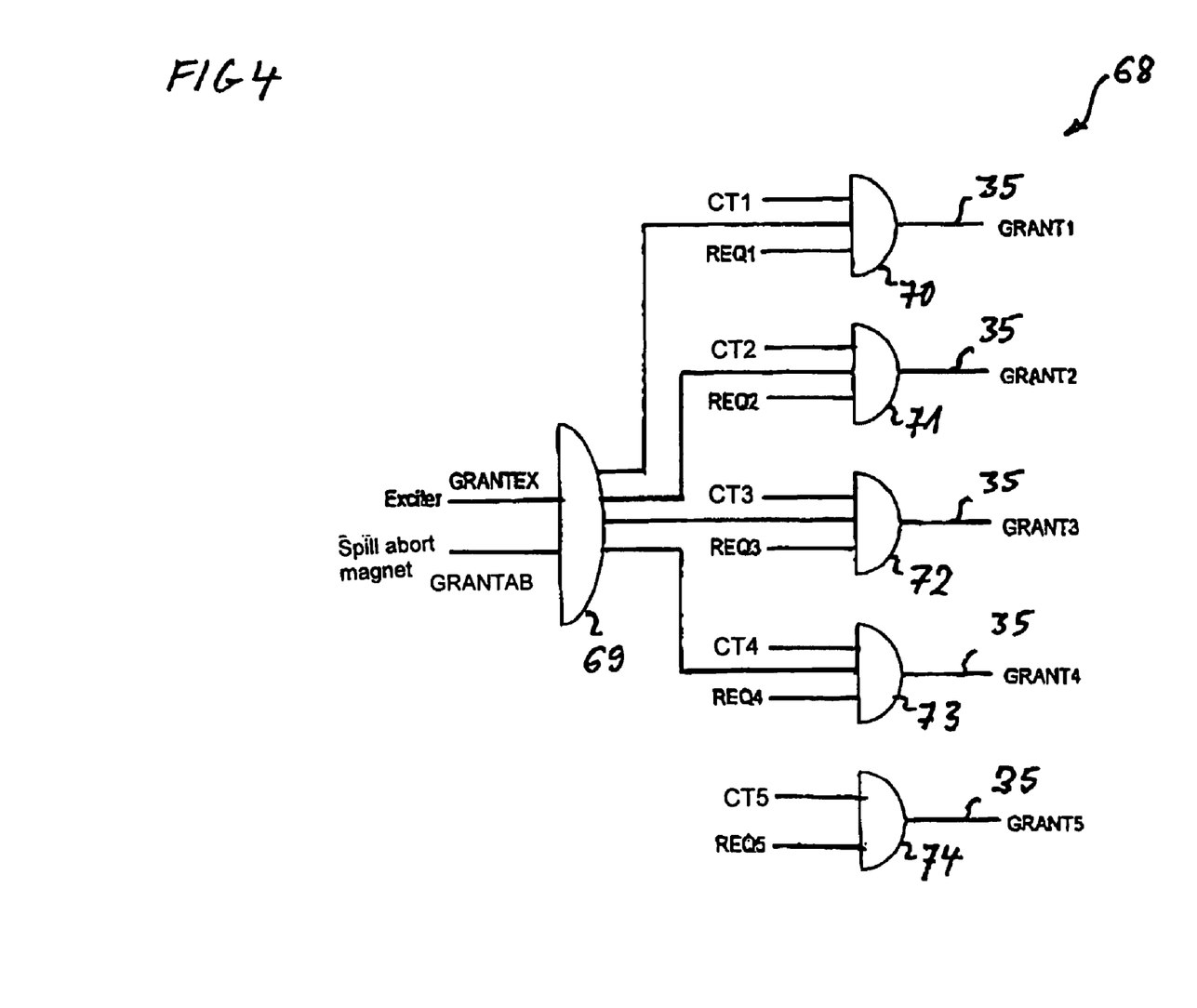
FIG. 4 is a generalised representation of a grant circuit for processing grant signals by way of grant lines.

FIG. 4 is a generalised representation of a grant circuit 68, wherein the information are then forwarded, by grant lines GRANTEX and GRANTAB, from the exciter and the spill abort magnet, respectively, of the spill abort system, by way of an ANDGATE 69, to appropriate ANDGATEs 70-73, which in addition to that input from the ANDGATE 69 have two further inputs, namely CT1 to CT4 and REQ1 to REQ4, which ensure both that a request signal is present at one of the inputs REQ1 to REQ2 and also that a signal for a confirmed active beam target is present at one of the inputs CT1 to CT4 of the four ANDGATEs 70-73, so that at the outputs of those ANDGATEs a signal GRANT1 to GRANT4 can be sent back to the control rooms by way of corresponding grant lines 35. The grant signal GRANT1 to GRANT5 presupposes a request at the inputs REQ1 to REQ5 of the ANDGATEs 70-74 and allocation by the arbitration unit at the inputs CT1 to CT5 of the ANDGATEs 70-74. Checking of the request signal is redundant at this point because allocation by the arbitration unit presupposes a request from the request entity of control room. The accelerator does not require a grant signal from the spill abort element, just allocation by the arbitration unit, which is, however, also signalled by way of the grant line GRANT5. By means of this grant circuit it is accordingly ensured in a manner relevant to safety that at a given time only one request entity or control room is given a grant signal by the arbitration unit by way of the grant lines 35 leading to one of the control rooms.

Figure 5:
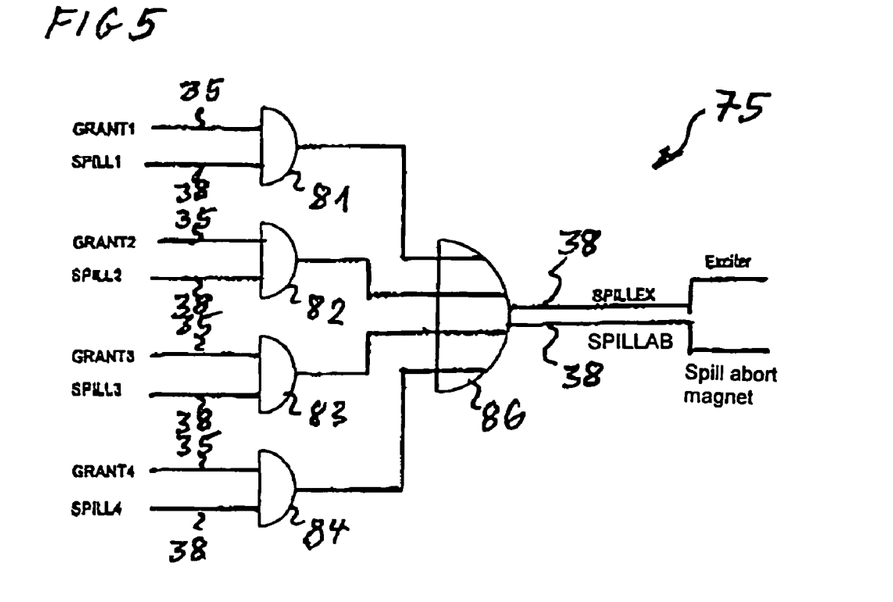
FIG. 5 is a generalised representation of a spill pause circuit for processing spill pause signals by way of spill pause lines.

FIG. 5 is a generalised representation of a spill pause circuit 75. This spill pause circuit 75 having the spill pause lines 38 can be used by all four control rooms of the three irradiation rooms and the one quality assurance room only when a grant signal GRANT1 to GRANT4 from the spill abort elements of the spill abort system is present. The spill pause circuit 75 accordingly has four ANDGATEs 81-84, each of which has two inputs for a grant signal GRANT1 to GRANT4 and a spill signal SPILL1 to SPILL4, those signals being applied to the ANDGATEs 81-84 by way of grant lines 35 and spill pause lines 38. The outputs of the ANDGATEs 81-84 lead to inputs of an ORGATE 86 which has two outputs SPILLEX and SPILLAB, which are connected, each by way of a spill pause line 38, to the exciter or spill abort magnet, respectively. When the accelerator has sovereignty, it directly controls the exciter and the spill abort magnet. The spill pause line 38 is accordingly not used by the accelerator. With the spill pause circuit 75 no differentiation is made as to whether the spill is being paused or is already at an end. The decision as to whether the residual beam in the acceleration region, the synchrotron, should be destroyed is taken solely by the accelerator control system in the corresponding control room.

Figure 6:
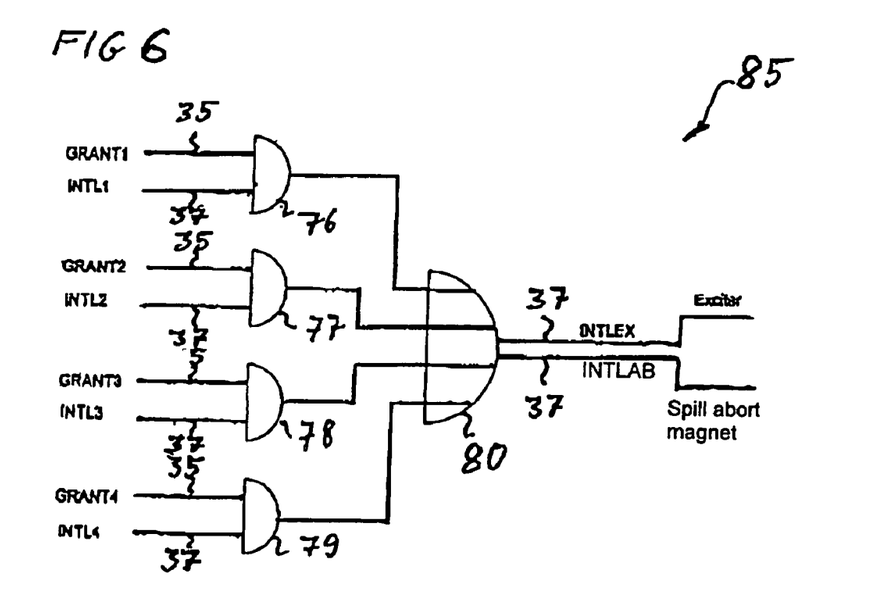
FIG. 6 is a generalised representation of an interlock circuit for processing interlock signals by way of interlock lines.

FIG. 6 shows a generalised representation of an interlock circuit 85 for the processing of interlock signals INTL1 to INTL4 by way of interlock lines 37 by means of AND-GATEs 76-79, to the inputs of which a grant signal GRANT1 to GRANT4 must simultaneously be supplied, by way of the grant lines 35, in order, by way of one of the outputs of the ANDGATEs 76-79, to achieve the input of an ORGATE 80. The ORGATE 80 in turn has two outputs INTLEX and INTLAB, which lead to the exciter and the spill abort magnet, respectively, by way of interlock lines 37. The interlock line 37 of the exciter and of the spill abort magnet can accordingly be used by all four irradiation positions only when the grant signal GRANT1 to GRANT4 from the spill abort elements is present. When the accelerator has sovereignty, it controls the exciter and the spill abort magnet directly so that interlock line 37 is not used by the accelerator.

Figure 7:
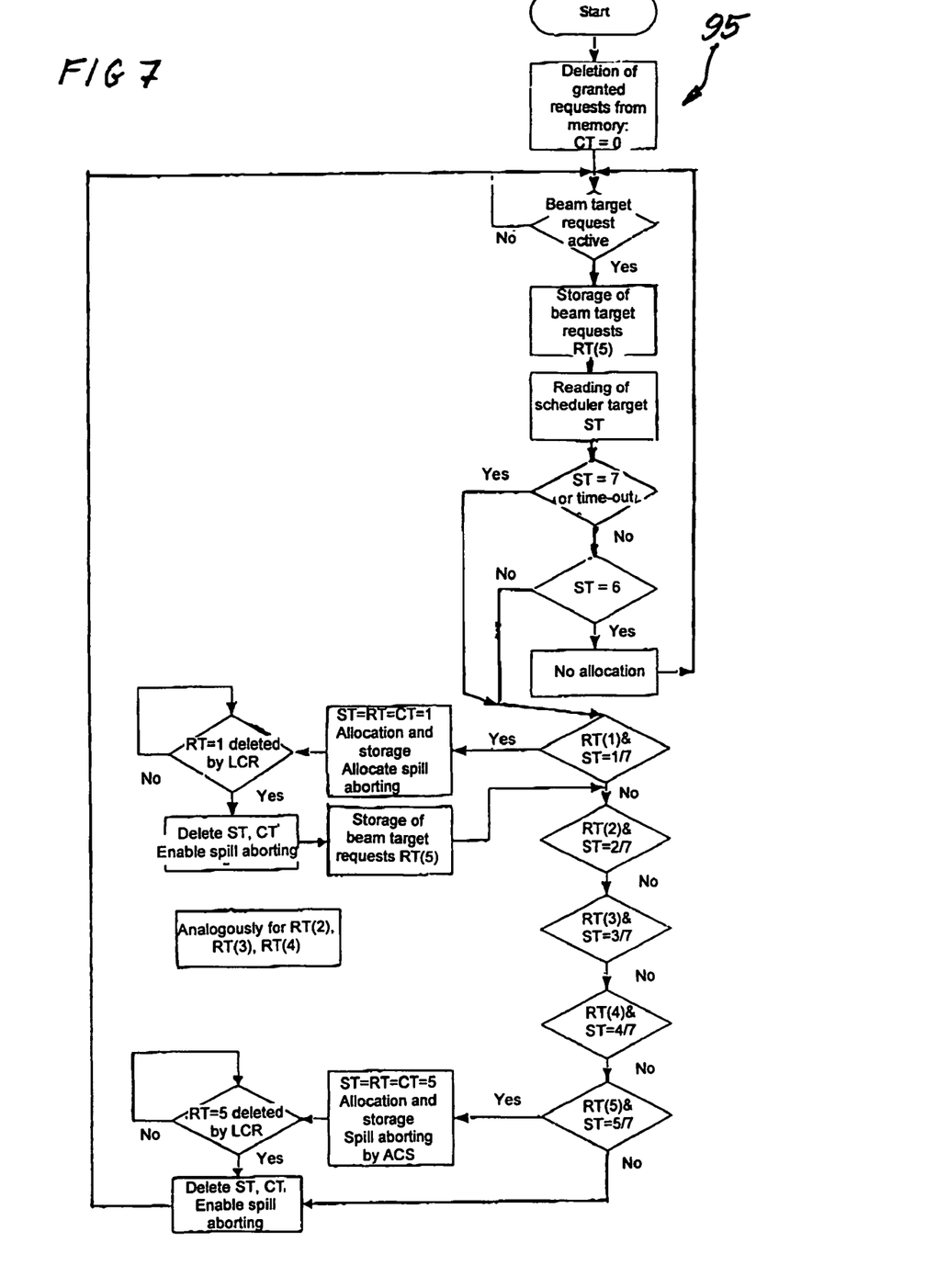
FIG. 7 is a schema of a flow diagram of a sequence control of an arbitration unit.

FIG. 7 is the schema of a flow diagram 95 of a sequence control of an arbitration unit. This flow diagram 95 takes into account the fact that a scheduler may be present or may not be. The path though the flow diagram 95 changes accordingly. In the flow diagram 95, the beam target instruction of the scheduler is defined by the reference letters ST, the requesting beam target or requesting control room is denoted by RT and a confirmed active beam target is indicated by the reference letters CT. This sequence control is received by the arbitration unit from the scheduler by way of a digital in/out module, the desired next request entity or the next requesting control room.

The request entities, which are indicated in the flow diagram 95 by RT1 to RT4, correspond to the irradiation rooms H1, H2, gantry and QA in the generalised circuit diagram shown in FIG. 1. The request entity RT5 corresponds to the accelerator, to which the beam guidance up to the beam destroyer of the accelerator and all irradiation positions enabled for the accelerator belong. The request entity ST6 means that, at the moment, sovereignty is not allocated, and the request entity ST7 means that the scheduler is not active and is not delivering instructions so that the arbitration unit allocates sovereignty independently. This allocation by the arbitration unit should then be carried out using a polling method wherein the arbitration unit gives the request units or control rooms, in turn, the opportunity of making a reservation.

The connection between the scheduler and the arbitration unit is safeguarded by means of suitable reserved direct lines or other mechanisms insofar as the arbitration unit recognises when the scheduler is not active and accordingly the read request entities are in any case invalid. In such a case, the procedure is as if the request entity ST7 had been read, which corresponds to an instruction to proceed according to a polling method. In addition, the absence of a the scheduler signals is visually displayed at the arbitration unit and likewise the status of all request, grant and interlock lines and the selected request entity in the case of an operating scheduler is made visible. Furthermore, the arbitration units have a local mode, in which in principle no attempt is made to read a request entity or control room from the scheduler so that a local switch likewise bring about allocation by the polling method. The status of the local switch in the control room in question is likewise visually displayed on the device.

The flow diagram 95 for the sequence control supplements the processing of request, grant and interlock signals, which have been described hereinbefore. The sequence control of the arbitration unit reads in accordance with the flow diagram 95 the request entity desired by the scheduler or corresponding control room, which is also referred to as the scheduler entity SE. As soon as beam sovereignty has been re-allocated, the irradiation entity IE is forwarded to the request and grant circuits and by that means ensures that only the selected position can reserve the spill abort elements. As soon as the reservation has been made, the sequence control of the arbitration unit has no more influence. In particular, the interlock signal is not influenced by the sequence control.

Figure 8:
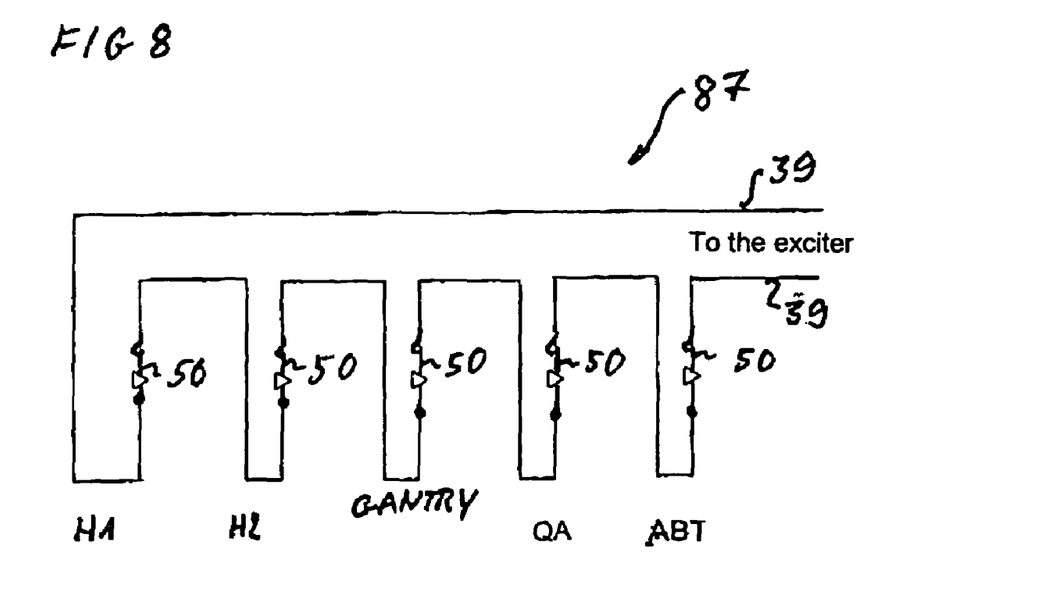
FIG. 8 is a generalised representation of the series connection of potential-free contacts of the control rooms for a spill abort by way of an exciter of the acceleration region.

FIG. 8 is a generalised representation of the series connection 87 of potential-free contacts 50 of the control rooms for a spill abort by means of an exciter of the acceleration region. The exciter is directly controlled from one of the control rooms by way of a redundant signal path 39 in order to bring about a beam abort within a few micro-seconds. For the purpose, there are located in the redundant signal path 39 breaker contacts 50 for the three control rooms having irradiation rooms H1, H2 and GANTRY and also for the quality assurance room QA and for the arbitration unit ABT, which likewise can provide the exciter for a rapid beam abort by way of the redundant signal path 39.

Figure 9:
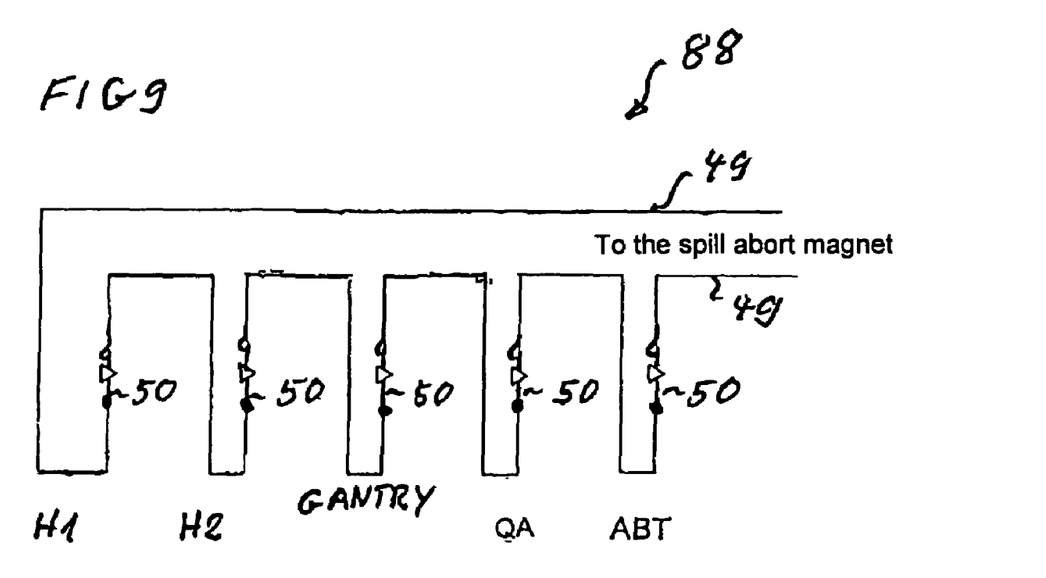
FIG. 9 is a generalised representation of the series connection of potential-free contacts of the controls for a spill abort by way of a spill abort magnet of the acceleration region.

FIG. 9 is a generalised representation of the series connection 88 of potential-free contacts 50 of the control rooms for a spill abort by means of a spill abort magnet of the acceleration region. The potential-free contacts 50 of the spill abort system are accordingly provided for each irradiation room or control room in duplicate for the exciter and the spill abort magnet. They can bring about the spill abort only once irradiation has been started at the irradiation position in question, not when there are no irradiation activities are taking place in the irradiation room. For the purpose, the individual potential-free contacts 50 of the irradiation positions are series-connected and are independent of the arbitration mechanism itself. However, the arbitration unit does have the possibility of also initiating a spill abort by this means by way of the redundant signal paths 39 or 49.

| List of reference symbols | |
|---|---|
| 1 | particle accelerator |
| 2 | accelerator ring |
| 3 | transport path |
| 4-7 | deflection components |
| 8 | control room, H1 |
| 9 | control room, H2 |
| 10 | control room, gantry |
| B11 | control room, QA |
| 12 | control room, accelerator |
| 13 | treatment room |
| 14 | treatment room |
| 15 | treatment room (gantry) |
| 16 | quality assurance room |
| 17 | particle beam |
| 18-20 | deflection magnet |
| 21 | beam allocation apparatus |
| 22-25 | collection chamber |
| 26 | arbitration unit |
| 27 | switching logic |
| 28 | monitoring unit |
| 29 | sequence control |
| 30 | signal line |
| 31 | spill abort system |
| 32 | spill abort magnet |
| 33 | exciter |
| 34 | request signal line |
| 35 | grant signal line |

-continued

| List of reference symbols | |
|---|---|
| 36 | clear signal line |
| 37 | interlock line |
| 38 | spill pause line |
| 39 | redundant signal path to exciter |
| 40 | input signal connection of the monitoring unit |
| 41 | input signal connection of the monitoring unit |
| 42 | interlock signal of the monitoring unit |
| 43 | interlock signal (potential-free) of the monitoring unit |
| 44 | interlock signal of the monitoring unit |
| 45 | interlock signal (potential-free) of the monitoring unit |
| 46 | scheduler |
| 47 | coupling-in region |
| 48 | coupling-out region |
| 49 | redundant signal path to the spill abort magnet |
| 50 | switching elements of a control room |
| 51 | signal bus of the control rooms |
| 52 | signal bus of the sequence control |
| 53 | signal bus of the scheduler |
| 54 | output signal line of the sequence control |
| 55 | output signal line of the scheduler |
| 56 | linear accelerator |
| 57 | request circuit |
| 58-62 | flip-flop of the request circuit |
| 63-66 | ANDGATEs of the request circuit |
| 67 | ORGATE of the request circuit |
| 68 | grant circuit |
| 69 | ANDGATE of the grant circuit |
| 70-74 | ANDGATEs of the grant circuit |
| 75 | spill pause circuit |
| 76-79 | ANDGATEs of the spill pause circuit |
| 80 | ORGATE of the spill pause circuit |
| 81-84 | ANDGATEs of the interlock circuit |
| 85 | interlock circuit |
| 86 | ORGATE of the interlock circuit |
| 87 | series switches to the exciter |
| 88 | series switches to the spill abort magnet |
| 89 | ion source |
| 95 | flow diagram |

The invention claimed is:

1. Beam allocation apparatus for medical particle accelerators, the particle accelerator having at least one acceleration region, a transport path and deflection components, by way of which a plurality of treatment rooms, each having a control room, are supplied with a particle beam comprising ion packets, wherein the beam allocation apparatus has an arbitration unit having switching logic, monitoring unit and sequence control, which is in electrical communication, by way of signal lines, with a spill abort system which has at least two rapid spill abort elements in the acceleration region and/or in the beam guidance common to all the irradiation positions, the beam allocation apparatus providing direct access from the control room of the irradiation-active treatment room for aborting the particle beam within micro-seconds in the event of danger.

2. Beam allocation apparatus according to claim 1, wherein the spill abort system has a spill abort magnet.

3. Beam allocation apparatus according to claim 1, wherein the beam allocation apparatus has access to an exciter.

4. Beam allocation apparatus according to claim 1, wherein each control room of a treatment room and/or of a quality assurance room, and also of the particle accelerator, has a request signal line to the switching logic of the arbitration unit for requesting transfer of beam sovereignty to the control room together with access entitlement to the exciter and/or the spill abort magnet of the acceleration region.

5. Beam allocation apparatus according to claim 1, wherein each control room of a treatment room and/or of a quality assurance room, and also of the particle accelerator, has a grant signal line to the switching logic of the arbitration unit for confirming transfer of access entitlement to the exciter and/or the spill abort magnet of the acceleration region for the control room during a phase of active irradiation.

6. Beam allocation apparatus according to claim 1, wherein each control room of a treatment room andlor of a quality assurance room has a clear signal line to the switching logic of the arbitration unit for confirming a completed irradiation abort and for deleting an access reservation to the exciter and/or the spill abort magnet of the acceleration region for the control room.

7. Beam allocation apparatus according to claim 1, wherein each control room of a treatment room and/or of a quality assurance room has an interlock line to the switching logic of the arbitration unit for aborting irradiation by means of direct access from the control room to the exciter and/or the spill abort magnet of the acceleration region.

8. Beam allocation apparatus according to claim 1, wherein each control room of a treatment room and/or of a quality assurance room has a spill pause line to the switching logic of the arbitration unit for aborting irradiation by means of direct access from the control room to the exciter and/or the spill abort magnet whilst maintaining an access reservation.

9. Beam allocation apparatus according to claim 1, wherein the switching logic of the arbitration unit has in each case a request signal line, a grant signal line, a spill pause line, an interlock line and a clear signal line, of which the switching logic is in electrical communication with the components of the spill abort system.

10. Beam allocation apparatus according to claim 1, wherein the monitoring unit of the arbitration unit receives signals, by way of input signal connections, from the switching logic and the sequence control and is connected, by way of output signal connections, to the spill abort system of the acceleration region.

11. Beam allocation apparatus according to claim 1, wherein a scheduler is connected to the switching logic of the arbitration unit and, by means of the sequence control of the arbitration unit, controls the working through of a queue of irradiation requests from the control rooms, which is produced in the scheduler.

12. Beam allocation apparatus according to claim 1, wherein the exciter is a high-frequency resonance component for ion packets in the coupling-in region of the accelerator and initiates a beam abort in microseconds as a result of variation or mismatching of the resonance tuning.

13. Beam allocation apparatus according to claim 1, wherein the spill abort magnet is a beam guidance magnet in the coupling-out region of the acceleration region.

14. Beam allocation apparatus according to claim 1, wherein the beam allocation apparatus has a control and management means for allocation of a particle beam of an irradiation system having an ion writing beam of an ion beam scanning apparatus for a target volume.

15. Beam allocation apparatus for medical particle accelerators, the particle accelerator having at least one acceleration region , a transport path and deflection components, by way of which a plurality of treatment rooms, each having a control room, are supplied with a particle beam comprising ion packets, wherein the beam allocation apparatus has an arbitration unit having switching logic, monitoring unit and sequence control, which is in electrical communication, by way of signal lines, with a spill abort system which has at least two rapid spill abort elements in the acceleration region and/or in the beam guidance common to all the irradiation positions, the control rooms being serially connected to the spill abort system by means of a potential-free interlock line, and the beam allocation apparatus providing direct access to the irradiation-active treatment room for aborting the particle beam within micro-seconds in the event of danger.

16. Beam allocation method for medical particle accelerators, the particle accelerator having at least one acceleration region, a transport path and deflection components, by way of which a plurality of treatment rooms, each having a control room, are sequentially supplied with a particle beam comprising ion packets, the beam allocation method comprising the following method steps:

requesting reservation, by one of the control rooms, of particle beam sovereignty, especially reservation of direct access to a spill abort system of the acceleration region required by all the treatment rooms, for a planned irradiation duration;

carrying out safety-relevant reservation of the spill abort system by an electronic switching logic of an arbitration unit;

reporting of the completed reservation to each control room with permission for only control room to carry out beam aborting by means of the spill abort system;

holding in a state of readiness, for the control rooms, a direct redundant signal path, which is independent of the arbitration unit,leading to the spill abort system of the acceleration system, the switching elements of the control rooms being connected in series, it being possible, in the event of simultaneous beam reservation requests from a plurality of control rooms, for the arbitration unit to decide which control room of an irradiation position can make the reservation and, it being possible, despite the loss of a reservation, for a spill abort to be initiated from each control room by way of the redundant signal path.

17. Beam allocation method according to claim 16, wherein beam sovereignty is transferred from an active control room to another control room only when the current control room actively relinquishes control over the particle beam.

18. Beam allocation method according to claim 16, wherein the spill abort system of the accelerator ring is activated for switching off the beam for a short period.

19. Beam allocation method according to claim 16, wherein a control room for the particle accelerator makes a reservation for the spill abort system once it has been ensured that either no beam is reaching the irradiation rooms or that no patient is present therein.

20. Beam allocation method according to claim 16, wherein the status of all reservations, access entitlements and acknowledgements are checked by a monitoring unit of the arbitration unit and, in the event of inconsistency, switching-off is carried out by way of the redundant signal path.

21. Beam allocation method according to claim 16, wherein, by means of a non-safety-relevant microprocessor system in the form of a scheduler, a sequence of reservation allocation of the spill abort system is reported to the arbitration unit and, when the microprocessor system is absent or when allocations are absent, the arbitration unit gives the control rooms, in turn, the opportunity to make a reservation.

* * * * *